United States Patent [19]

Loh

[11] 4,432,786
[45] Feb. 21, 1984

[54] THIENYLMETHOXYIMINOALKYL CYCLOHEXANEDIONE HERBICIDES

[75] Inventor: William Loh, Petaluma, Calif.

[73] Assignee: Chevron Research Company, San Francisco, Calif.

[21] Appl. No.: 376,325

[22] Filed: May 10, 1982

[51] Int. Cl.³ .................. A01N 43/02; C09B 23/16
[52] U.S. Cl. .................................. 71/90; 542/414; 549/63; 549/65; 549/68; 549/75; 549/76
[58] Field of Search ............ 71/90; 549/75, 63, 65, 549/68, 76; 542/414

[56] References Cited

U.S. PATENT DOCUMENTS

| | | | |
|---|---|---|---|
| 3,989,737 | 11/1976 | Sawaki et al. | 549/75 |
| 4,116,974 | 9/1978 | Farge et al. | 71/90 |
| 4,188,203 | 2/1980 | Farge et al. | 71/90 |

Primary Examiner—Alan Siegel
Attorney, Agent, or Firm—D. A. Newell; T. G. De Jonghe; L. S. Squires

[57] ABSTRACT

Compounds of the formula:

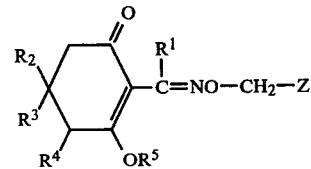

wherein $R^1$ is H or alkyl; $R^2$ and $R^3$ are independently H, alkyl, aryl or substituted aryl; $R^4$ is H or alkoxycarbonyl; $R^5$ is H, acyl or a cation; and Z is thienyl or substituted thienyl.

The compounds exhibit grass herbicide activity and are prepared via the reaction of the appropriately substituted cyclohexane-1,3-dione with the appropriate thienylmethoxyamine derivative and optionally acylating this product at the 3-hydroxy position or converting it to the cation salt.

28 Claims, No Drawings

THIENYLMETHOXYIMINOALKYL CYCLOHEXANEDIONE HERBICIDES

BACKGROUND OF THE INVENTION

1. Field of the Invention

This invention relates to a 2-[1-(thienylmethoxyimino)alkyl]-cyclohexane-1,3-diones and derivatives thereof and intermediates therefor. In a further aspect, the invention relates to herbicidal compositions and fungicidal compositions containing such compounds and to the use of such compounds and compositions as herbicides and fungicides. In another aspect, the invention relates to processes for preparing such compounds, intermediates and compositions.

A number of 2-iminoalkylcyclohexane-1,3-dione derivatives having herbicidal activity are described in U.S. Pat. Nos. 3,943,176; 3,950,420; 3,989,737; 4,011,256; 4,033,754; and 4,249,937; and in assignee's copending application of Ta Tao Luo, U.S. Ser. No. 210,206, filed Nov. 25, 1980.

SUMMARY OF THE INVENTION

The present invention provides compounds which exhibit excellent grass herbicidal activity. In addition, certain of the compounds exhibit exceptional post-herbicidal activity at even low dosages against Wild Oats and yet are safe for use with wheat crops. This is especially advantageous as Wild Oats are very difficult to safely remove chemically from wheat crops. A number of the compounds also exhibit a modest degree of fungicidal activity against Celery Late Blight pathogenic fungi. The compounds of the present invention can be represented by the following generic formula:

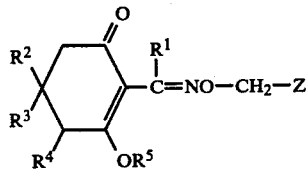

wherein
$R^1$ is hydrogen or lower alkyl;
$R^2$ and $R^3$ are independently selected from the group consisting of hydrogen, lower alkyl, aryl having 6 through 10 carbon atoms (preferably phenyl), substituted aryl having 6 through 10 carbon atoms (preferably phenyl) and 1 through 4 substituents (preferably 1 or 2) independently selected from the group consisting of fluoro, chloro, bromo, iodo, or trifluoromethyl;
$R^4$ is hydrogen or alkoxycarbonyl having 2 through 4 carbon atoms;
$R^5$ is hydrogen, or an acyl group having 1 through 12 carbon atoms; and
Z is a group having the formula:

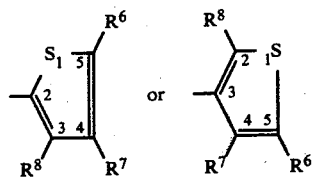

wherein $R^6$, $R^7$, and $R^8$ are independently selected from the group of hydrogen, halo, nitro, alkyl having 1 through 4 carbon atoms, alkoxy having 1 through 4 carbon atoms, or trifluoromethyl.

The salts of the compounds of Formula (I) (e.g., wherein $R^5$ is a cation) are also encompassed within the invention.

The compounds of the invention exist as tautomers. Also, where the compounds have an asymetric carbon atom, the compound may also exist as optical isomers. The above formula is intended to encompass all the existing tautomer and isomer forms and are encompassed within the present invention.

In another embodiment, the invention comprises herbicidal compositions comprising an herbicidally effective amount of the present compounds.

In another embodiment, the invention comprises the prevention, reduction and/or control of undesired vegetation, especially grasses, via the application of an herbicidally effective amount of the present compounds.

In still another embodiment, the invention provides a process for preparing the present compounds which comprises contacting the corresponding 2-($R^1$-carbonyl)-3-hydroxy-cyclohex-2-en-1-one derivative with the corresponding thienylmethoxyamine derivative under reactive conditions to yield the corresponding compound of Formula (I) and optionally treating this product with a basic inorganic salt or organic salt or an acyl halide to yield the corresponding $R^5$ salt or ester, respectively.

The invention will be further described hereinbelow.

FURTHER DESCRIPTION OF THE INVENTION AND PREFERRED EMBODIMENTS

Typical illustrations of the compounds of the invention can be had by reference to Examples 1-6 on Pages 12-15, hereinbelow. In terms of the substituents, the preferred compounds are those wherein $R^1$ is ethyl and propyl; and/or $R^2$ is methyl; and/or $R^3$ is methyl; and/or $R^4$ is hydrogen or methoxycarbonyl; and/or $R^5$ is hydrogen; and/or one of $R^6$, $R^7$, or $R^8$ is chloro and preferably the others are hydrogen. The compound of the invention wherein $R^1$ is propyl, $R^2$ is methyl, $R^3$ is methyl, $R^4$ is hydrogen, and Z is 5-chlorothien-2-yl has been found to exhibit very good post-herbicidal activity against Wild Oats while being safe for application in wheat crops at such dosages.

Definitions

As used herein, the following terms have the following meanings, unless expressly stated to the contrary.

The term "alkyl" refers to both straight- and branched-chain alkyl groups.

The term "lower alkyl" refers to both straight- and branched-chain alkyl groups having a total from 1 through 6 carbon atoms and includes primary, secondary and tertiary alkyl groups. Typical lower alkyls include, for example, methyl, ethyl, n-propyl, isopropyl, n-butyl, t-butyl, n-hexyl, and the like.

The term "alkylene" or "alkylidenyl" refers to both straight- and branched-chain alkylene groups.

The term "lower alkylene" refers to alkylene groups having from 1 through 6 carbon atoms. Typical alkylene groups include, for example, methylene, ethylene, or ethylidenyl (i.e., =CH—CH₂=), 2-methylpropylene $$\text{(i.e., } -CH_2-\underset{\underset{CH_3}{|}}{CH_2}-CH_2-\text{),}$$

and the like.

The term "alkenyl" refers to unsaturated alkyl groups having a double bond (e.g., $CH_3CH=CH(CH_2)_2-$,) and includes both straight- and branched-chain alkenyl groups.

"Lower alkenyl" groups refer to alkenyl groups having from 2 through 6 carbon atoms. Typical lower alkenyl groups include, for example, ethylene, but-3-enyl, hex-4-enyl, 2-methylpent-4-enyl, and the like.

The term "alkynyl" refers to unsaturated alkyl groups having a triple bond (e.g., $CH_3C\equiv C(CH_2)_2-$) and includes both straight- and branched-chain alkynyl groups.

The term "halo" or "halogen atom" refers to the groups fluoro, chloro, bromo and iodo.

The term "alkoxy" refers to the group $R^1O-$ wherein $R^1$ is alkyl.

The term "lower alkoxy" refers to alkoxy groups having from 1 through 6 carbon atoms and includes, for example, methoxy, ethoxy, t-butoxy, hexoxy, and the like.

The term "aryl" refers to aryl groups having from 6 through 10 carbon atoms and includes, for example, phenyl, naphthyl, and the like.

The term "acyl" refers to acyl groups derived from carboxylic acids having from 1 through 12 carbon atoms such as, for example, formyl, acetyl, propionyl, butyryl, valeryl, isovaleryl, hexanoyl, heptanoyl, octanoyl, nonanoyl, undecanoyl, lauroyl, benzoyl, phenylacetyl, phenylpropionyl, o-, m-, p-toluoyl, β-cyclopentylpropionyl, and the like.

The term "alkoxycarbonyl" refers to groups having the formula $$\underset{\underset{}{}}{R''O}\overset{\overset{O}{\|}}{C}-$$

wherein $R''$ is an alkyl group having from 1 through 11 carbon atoms. Typical alkoxycarbonyl groups thus include, for example, methoxycarbonyl, propoxycarbonyl, isopropoxycarbonyl, undecanoxycarbonyl, and the like. Alkoxycarbonyl having 2 through 4 carbon atoms, refers to the group of methoxycarbonyl, ethoxycarbonyl, propoxycarbonyl, or isopropoxycarbonyl.

With respect to the salts of Formula (I), the term "cation" refers to both inorganic and organic cations and preferably do not significantly adversely affect the herbicidal or environmental properties of the parent compound. Such cations include, for example, alkali metal cations (e.g., sodium and potassium), alkali earth metal cations (e.g., calcium), ammonium, tetraethyl ammonium, choline, and the like.

Synthesis

The compounds of the present invention wherein $R^5$ is hydrogen can be prepared via the following process schematically represented by the following overall reaction equation:

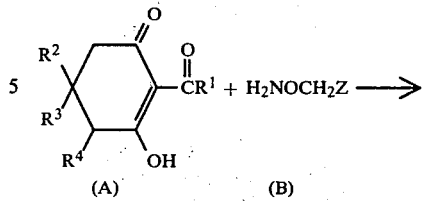

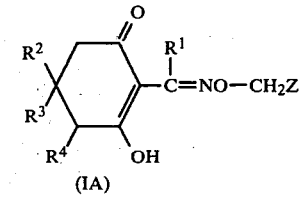

wherein $R^1$, $R^2$, $R^3$, $R^4$ and Z are as defined hereinabove.

This process can be conveniently effected by contacting Compound (A) with Compound (B) preferably in an inert organic solvent under reactive conditions. Typically, this process is conducted at temperatures in the range of about from 0° to 110° C., preferably about 10° to 50° C., for about from 6 to 24 hours, using about from 1.0 to 1.25, and preferably about from 1.0 to 1.1, mols of Compound (B) per mol of Compound (A). The reaction is typically conducted as a liquid-phase reaction and reaction pressure is generally not material except as it effects boiling points. Conveniently, the process is conducted at atmospheric or ambient pressure.

Suitable, inert organic solvents which can be used include, for example, ethyl alcohol, methyl alcohol, isopropyl alcohol, ethyl acetate, toluene, tetrahydrofuran, methylene chloride, and the like and compatible mixtures thereof. Typically, best results are obtained by conducting the process at 20° to 25° C., for about 18 to 24 hours, using 1.0 to 1.1 mols of Compound (B) per mol of Compound (A), and ethyl alcohol as a solvent.

Also, the acid salt of the compound of Formula (B) can be used and then converted in situ to the free amine via treatment with a base, preferably an alkali metal oxide.

The compounds of Formula (I) wherein $R^5$ is an acyl group can be prepared by treating the corresponding compound of Formula (IA) with the appropriate acyl halide (e.g., acyl chloride). This can be conveniently effected by contacting Compound (IA) with the acyl chloride at temperatures in the range of about 0° to 80° C. using about 1.0 to 1.25 mols of acyl halide per mol of Compound (IA), preferably in an inert organic solvent such as, for example, methylene chloride or ethyl acetate.

The salts of Formula (I) (e.g., wherein $R^5$ is a cation) can be prepared via neutralization of the $R^5$ hydroxy moiety in the corresponding Compound (IA) with the appropriate base, an alkali metal oxide. Additional variation in the cation, if desired, can be effected by ion exchange.

The starting materials of Formula (A) can be prepared via known procedures such as by the acylation of a 1,3-cyclohexanedione derivative, having the appropriate 4,5,5-substitution, with the desired $R^1$ acyl halide. Such procedures are known to the art and are, for example, described in Pages 3-8 of the aforementioned U.S. Ser. No. 210,206, filed Nov. 25, 1980, which procedures are hereby incorporated by reference and in SYNTHE- SIS, *A New Simple Synthesis of 2-Acylcyclohexane*-1,3-*diones*, 925, December 1978.

The starting materials of Formula (B) can be made via the reaction of a thienylmethyl halide (e.g., chloride) having the appropriate thienyl substitution with N-hydroxyphthalimide to yield the corresponding N-thienylmethoxyphthalimide which can then be treated with hydrazine to yield Compound (B). This can be represented by the following reaction sequence:

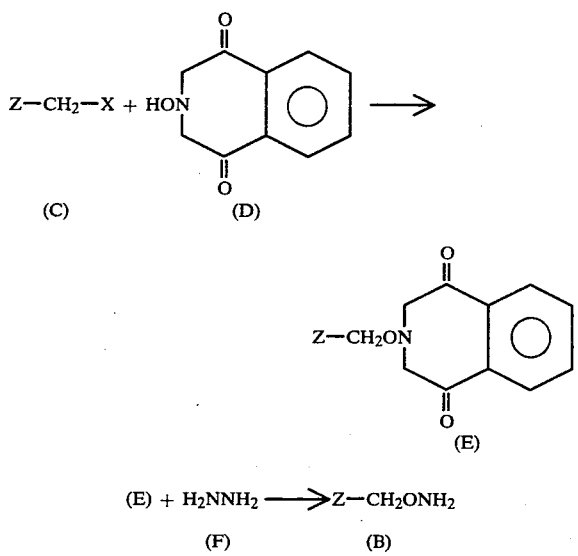

(E) + H$_2$NNH$_2$ $\longrightarrow$ Z—CH$_2$ONH$_2$ (F)　　　　　　　(B)

wherein X is halo, preferably Cl or Br, and Z is as defined hereinabove.

The first step of this process is an alkylation reaction and can be effected by contacting Compound (C) with N-hydroxyphthalimide (D) preferably in an inert organic solvent in the presence of a weak base to neutralize the hydrogen halide by-product. This step is typically conducted at temperatures in the range of about from 0° to 100° C., for about 2 to 24 hours, using about from 1.0 to 1.1 mols of Compound (C) per mol of Compound (D). Suitable inert organic solvents which can be used include, for example, dimethylsulfoxide, acetonitrile, dimethylformamide, and the like and compatible mixtures thereof. Suitable bases which can be used include, for example, potassium, carbonate, triethylamine, sodium hydroxide, and the like. N-hydroxyphthalimide is a known compound and can be prepared by known procedures. The thienylmethyl halides of Formula (C) also are generally known compounds and can be prepared by known procedures or by obvious modifications of such procedures using appropriate solvents and appropriately substituted substrates. Such procedures are, for example, described in the following journals and U.S. Patents: K. B. Wiberg and H. F. McShane, *Organic Synthesis,* Coll. Vol. III, 197 (1955); E. Campaigne and William M. Lesuer, *J. Amer. Chem. Soc.,* 70, 1555 (1948); E. Campaigne and W. M. Lesuer, *J. Amer. Chem. Soc.,* 71, 333 (1949); and U.S. Pat. Nos. 2,623,049 and 2,776,980.

The second step of this process can be effected by contacting Compound (E) with hydrazine (F) preferably in an inert organic solvent. This step is typically conducted at temperatures in the range of about from 50° to 80° C., for about from 1 to 5 hours, using about from 1 to 1.25 mols of hydrazine per mol of Compound (E). Conveniently lower alkanols such as ethanol can be used as an inert organic solvent. In some instances, it may be convenient to quench the reaction, after completion, with a mineral acid (e.g., HCl). In this case, the corresponding salt of Compound (B) will be formed which can be neutralized in situ in the principle reaction of Compounds (A) and (B), previously described hereinabove.

In the above-described processes, it is generally preferable to separate the respective products before proceeding with the next step in the reaction sequence unless expressly stated otherwise. These products can be recovered from their respective reaction product mixtures by any suitable separation and purification procedure, such as, for example, recrystallization and chromatography. Suitable separation and purification procedures are, for example, illustrated in the Examples set forth hereinbelow. Also, generally the reactions are conducted as liquid phase reactions and pressure is generally not significant except as it affects temperature where reactions are conducted at reflux.

It should also be appreciated that where typical preferred process conditions (e.g., reaction temperatures, times, mol ratios of reactants, solvents, etc.) have been given, that other process conditions could also be used, although typically with poor yields or economies. Optimum reaction conditions (e.g., temperature, reaction time, mol ratios, solvents, etc.) may vary with the particular reagents or organic solvents used but can be determined by routine optimization procedures.

If desired, the respective optical isomers of Formula (I) can be obtained by conventional resolution procedures, for example, by reacting the isomer mixture with an optically active acid which will yield a mixture of optical salts, of the desired compound, which can be resolved by conventional procedures (e.g., crystallization) into the respective plus and minus optical salts.

Utility

The compound of Formula (I) and its salts exhibit pre- and post-emergent herbicidal activity against grasses. In addition, by proper dosage control, this activity is selective to grasses and permits the use of the present compounds to control grasses which are present with broad-leaf plants and certain grass crops (e.g., wheat) without significantly injurying the broad-leaf plants or the grass crop.

Generally, for post-emergent applications, the herbicidal compounds are applied directly to the foliage or other plant parts. For pre-emergence applications, the herbicidal compounds are applied to the growing medium, or prospective growing medium, of the grass. The optimum amount of the herbicidal compound or composition will vary with the particular grass species, and the extent of plant growth and the particular part of the plant which is contacted. The optimum dosage will also vary with the general location, or environment, of application (e.g., sheltered areas such as greenhouses compared to exposed areas such as fields), and type and degree of control desired. Generally, for both pre- and post-emergent control, the present compounds are applied at rates of about from 0.2 to 60 kg/ha, preferably about from 0.5 to 10 kg/ha.

Also, although in theory the compounds can be applied undiluted, in actual practice they are generally applied as a composition or formulation comprising an effective amount of the compound(s) and an acceptable carrier. An acceptable carrier (agriculturally acceptable carrier) is one which does not significantly adversely affect the desired biological effect achieved by the active compounds, save to dilute it, and is generally nontoxic to the environment in the amounts used. Typically, the composition contains about from 0.01 to 95% by weight of the compound of Formula (I). Concentrates can also be made having higher concentrations designed for dilution prior to application. The carrier can be a solid, liquid, or aerosol. The actual compositions can take the form of granules, powders, dusts, solutions, emulsions, slurries, aerosols, and the like.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seed hulls, wheat flour, wood flour, wood bark flour, and the like can also be used as carriers. Suitable liquid diluents which can be used include, for example, water, organic solvents (e.g., hydrocarbons such as benzene, toluene, dimethylsulfoxide, kerosene, diesel fuel, fuel oil, petroleum naphtha, etc.), and the like. Suitable aerosol carriers which can be used include conventional aerosol carriers such as halogenated alkanes, etc.

The composition can also contain various promoters and surface-active agents which enhance the rate of transport of the active compound into the plant tissue such as, for example, organic solvents, wetting agents and oils, and in the case of compositions designed for pre-emergence application agents which reduce the leachability of the compound. The composition can also contain various compatible adjuvants, stabilizers, conditioners, insecticides, fungicides, and if desired, other herbicidally active compounds.

A further understanding of the invention can be had in the following non-limiting Preparations and Examples. Wherein, unless expressly stated to the contrary, all temperatures and temperature ranges refer to the Centigrade system and the term "ambient" or "room temperature" refers to about 20°–25° C. The term "percent" or "%" refers to weight percent and the term "mol" or "mols" refers to gram mols. The term "equivalent" refers to a quantity of reagent equal in mols, to the mols of the preceding or succeeding reactant recited in that example in terms of finite mols or finite weight or volume. Also, unless expressly stated to the contrary, geometric isomer and racemic mixtures are used as starting materials and correspondingly, isomer mixturs are obtained as products.

Preparation A

In this preparation, a mixture containing 73.41 gms (0.45 mol) of N-hydroxyphthalimide, 105.76 gms (0.50 mol) of 2-chloro-3-bromomethylthiophene and 69 gms (0.50 mol) of potassium carbonate in 500 mls of dimethylsulfoxide was stirred for about 12 hours at room temperature and then poured into ice-$H_2O$. The product was collected by filtration, washed with $H_2O$ and the residue was then recrystallized from ethanol affording 104.7 gms of N-(2-chlorothien-3-yl)methoxyphthalimide, m.p. 155°–156° C.

44 gms (0.15 mol) of N-(2-chlorothien-3-yl)methoxyphthalimide was mixed with 5.8 gms (0.17 mol) of 95% hydrazine in 600 mls of ethanol and refluxed for 2 hours. After cooling to room temperature, the solution was filtered, and the filtrate was concentrated under reduced pressure. The residue was treated with methylene chloride, filtered, and concentrated again under reduced pressure, affording O-[(2-chlorothien-3-yl)methyl]hydroxylamine.

Similarly, by following the same procedure, using the appropriate starting materials, the following compounds are respectively prepared:
O-(thien-3-ylmethyl)hydroxylamine;
O-(thien-2-ylmethyl)hydroxylamine;
O-[(5-chlorothien-2-yl)methyl]hydroxylamine;
O-[(3,5-dichlorothien-2-yl)methyl]hydroxylamine; and
O-[(2,5-dichlorothien-3-yl)methyl]hydroxylamine.

EXAMPLE 1

In this example, a mixture containing 4.0 gms (0.02 mol) of 5,5-dimethyl-3-hydroxy-2-propionylcyclohex-2-en-1-one and 3.6 gms (0.022 mol) of O-[(5-chlorothien-2-yl)methyl]hydroxylamine in 75 mls of ethanol was stirred at room temperature for about 12 hours. The mixture was then evaporated to remove the ethanol, affording a thick syrup. The syrup was then dissolved in methylene chloride and extracted twice with aqueous 5% wt. sodium hydroxide. The aqueous layer was separated and acidified with concentrated hydrochloric acid and then extracted twice with methylene chloride. The methylene chloride layer was separated, dried with magnesium sulfate, and filtered. The filtrate was evaporated under vacuum, affording a viscous liquid which was then purified via column chromatography eluting with tetrahydrofuran-hexane (1:2 vol. ratio) affording 4.8 gms of 2-{1-[(5-chlorothien-2-ylmethoxy)imino]-propyl}-3-hydroxy-5,5-dimethylcyclohex-2-en-1-one.

Similarly, by following the same procedure using the corresponding cyclohexane-1,3-dione derivative, the following compounds are respectively prepared:
2-{1-[(5-chlorothien-2-ylmethoxy)imino]methyl}-3-hydroxy-5,5-diphenylcyclohex-2-en-1-one;
2-{1-[(5-chlorothien-2-ylmethoxy)imino]propyl}-3-hydroxy-5-(4-trifluoromethylphenyl)-cyclohex-2-en-1-one;
2-{1-[(5-chlorothien-2-ylmethoxy)imino]pentyl}-3-hydroxy-5-(2-chloro-4-fluorophenyl)-5-(trifluoromethylphenyl)-cyclohex-2-en-1-one; and
2-{1-[(5-chlorothien-2-ylmethoxy)imino]hexyl}-3-hydroxy-5,5-(2-chloronaphthyl)-cyclohex-2-en-1-one.

Similarly, by following the same procedure but respectively replacing O-[(5-chlorothien-2-yl)methyl]hydroxylamine with O-(thien-2-ylmethyl)hydroxylamine; O-[(5-fluorothien-2-yl)methyl]hydroxylamine; O-[(4-nitrothien-2-yl)methyl]hydroxylamine; O-[(4,5-dimethylthien-2-yl)methyl]hydroxylamine; O-[(5-methoxythien-2-yl)methyl]hydroxylamine; O-[5-trifluoromethylthien-2-yl)methyl]hydroxylamine; and O-[(3-chloro-4-nitro-5-trifluoromethylthien-2-yl)methyl]hydroxylamine, the corresponding thien-2-yl; 5-fluorothien-2-yl; 4-nitrothien-2-yl; 4,5-dimethylthien-2-yl; 5-methoxythien-2-yl; 5-trifluoromethylthien-2-yl; and 3-chloro-4-nitro-5-trifluoromethylthien-2-yl analogs of each of the above products are respectively prepared.

EXAMPLE 2

In this example, a mixture containing 4.2 gms (0.02 mol) of 5,5-dimethyl-3-hydroxy-2-butyrylcyclohex-2-en-1-one and 2.84 gms (0.022 mol) of O-(thien-3-ylmethyl)hydroxylamine in 75 mls of ethanol was stirred at room temperature for about 12 hours. The mixture was then evaporated to remove the ethanol, affording a thick syrup. The syrup was then dissolved in methylene chloride and extracted twice with aqueous 5% wt. sodium hydroxide. The aqueous layer was separated and acidified with concentrated hydrochloric acid and then extracted twice with methylene chloride. The methylene chloride layer was separated, dried with magnesium sulfate, and filtered. The filtrate was evaporated under vacuum, affording a clear liquid which was then purified via column chromatography eluting with tetrahydrofuran-hexane (1:2) affording 5.3 gms of 2-{1-[(thien-3-ylmethoxy)imino]butyl}-3-hydroxy-5,5-dmethylcyclohex-2-en-1-one.

Similarly, by following the same procedure using the corresponding cyclohexane-1,3-dione derivative, the following compounds are respectively prepared:
2-{1-[(thien-3-ylmethoxy)imino]methyl}-3-hydroxy-5,5-diphenylcyclohex-2-en-1-one;
2-{1-[(thien-3-ylmethoxy)imino]propyl}-3-hydroxy-5-(4-trifluoromethyl-2-chlorophenyl)-cyclohex-2-en-1-one;
2-{1-[(thien-3-ylmethoxy)imino]pentyl}-3-hydroxy-5-(2-bromo-3-chloropheny)-5-(trifluoromethylphenyl)-cyclohex-2-en-1-on; and
2-{1-[(thien-3-ylmethoxy)imino]hexyl}-3-hydroxy-5,5-(2-trifluoromethylnaphthyl)-cyclohex-2-en-1-one.

Similarly, by following the same procedure but respectively replacing O-[(5-chlorothien-3-yl)methyl]hydroxylamine with O-(thien-3-ylmethyl)hydroxylamine; O-[(5-bromothien-3-yl)methyl]hydroxylamine; O-[(4-nitrothien-3-yl)methyl]hydroxylamine; O-[(2-ethylthien-3-yl)methyl]hydroxylamine; O-[(5-methoxythien-3-yl)methyl]hydroxylamine; O-[(2-trifluoromethylthien-3-yl)methyl]hydroxylamine; O-[(2-bromo-4-nitro-5-trifluoromethylthien-3-yl)methyl]hydroxylamine, the corresponding thien-3-yl; 5-bromothien-3-yl; 4-nitrothien-3-yl; 2-ethylthien-3-yl; 5-methoxythien-3-yl; 2-trifluoromethylthien-3-yl; and 2-bromo-4-nitro-5-trifluoromethylthien-3-yl analogs of each of the above products are respectively prepared.

EXAMPLE 3

This example illustrates the preparation of the acyloxy compounds of the invention.

To a reaction mixture containing 3.6 gms (0.01 mol) of 2-{1-[(5-chlorothien-2-ylmethoxy)imino]butyl}-3-hydroxy-5,5-dimethylcyclohex-2-en-1-one and 0.87 gm (0.011 mol) of pyridine in 20 mls of methylene chloride stirred at 0° C. is added 0.89 gm (0.011 mol) of acetyl chloride. The mixture is then stirred at room temperature for 2 hours. The mixture is then worked up by washing with water, drying with anhydrous magnesium sulfate, and filtered. The filtrate is evaporated under vacuum affording 3-acetyloxy-2-{1-[(5-chlorothien-2-ylmethoxy)imino]butyl}-5,5-dimethylcyclohex-2-en-1-one.

Similarly, by following the same procedure, the corresponding 3-acetyloxy derivative of each of the products of Examples 1 and 2 are respectively prepared.

EXAMPLE 4

This example illustrates the preparation of the salts of the present invention.

To 3.6 gms (0.01 mol) of 2-{1-[(5-chlorothien-2-ylmethoxy)imino]butyl}-3-hydroxy-5,5-dimethylcyclohex-2-en-1-one in 10 mls of acetone is added 0.4 gm (0.01 mol) of sodium hydroxide dissolved in 2 mls of water. The solvents are evaporated under vacuum affording the 3-hydroxy sodium salt of 2-{1-[(5-chlorothien-2-ylmethoxy)imino]butyl}-3-hydroxy-5,5-dimethylcyclohex-2-en-1-one.

Similarly, by following the same procedure, the sodium salts of each of the products of Examples 1 and 2 are respectively prepared.

EXAMPLE 5

Similarly, by following the same general procedures as described in Preparation A and Examples 1 and 2 hereinabove, but using the appropriate bromo or chloromethylthiophene position isomer having the appropriate substitution in Preparation A, and the corresponding cyclohexane-1,3-dione derivative having the appropriate substitution, the compounds identified in Tables A, B and C of Example 6 hereinbelow were prepared.

EXAMPLE 6

In this example, a number of the compounds of the present invention were respectively tested for pre-emergent and post-emergent activity against a variety of grasses and broad-leaf plants including one grain crop and one broad-leaf crop. The compounds tested are identified in Tables A, B and C hereinbelow.

Pre-Emergent Herbicide Test

Pre-emergence herbicidal activity was determined in the following manner.

A stock solution of the test compound was prepared by admixing 2 mls of acetone containing 110 gms of a nonionic surfactant to a solution containing 355.5 mgs of test compound dissolved in 15 mls of acetone. Twelve mls of this stock solution were added to 47.7 mls of water containing the same surfactant at a concentration of 625 mgs/l.

Seeds of the test vegetation were planted in a pot of soil and the cyclohexanedione test solution was sprayed uniformly onto the soil surface at a dose of 27.5 micrograms/$cm^2$. The pot was watered and placed in a greenhouse. The pot was watered intermittently and was observed for seedling emergence, health of the emerging seedlings, etc., for a 3-week period. At the end of this period, the herbicidal effectiveness of the test compound ws rated based on the physiological observations. A 0-to-100 scale was used, 0 representing no phytotoxicity and 100 representing complete kill. The results of these tests are summarized in Table 1, hereinbelow.

Post-Emergent Test

The test compound was formulated in the same manner as described above for the pre-emergent test. This formulation was uniformly sprayed on 2 similar pots containing plants 2 to 3 inches tall (except Wild Oats, Soybean and Watergrass which were 3 to 4 inches tall) (approximately 15 to 25 plants per pot) at a dose of 27.5 micrograms/$cm^2$. After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity and 100 representing complete kill. The results of these tests are summarized in Table 2.

Certain of these compounds were then tested for post-emergence activity at very low dosages to determine at what dosage activity would break and selectivity for grasses versus broad-leaf plants. These tests were conducted in the same manner as described above with the exception of the dosage used. The results of these tests and the dosages used are summarized in Tables 2 and 3 hereinbelow.

As can be seen from Tables 2 and 3, the compounds of the invention exhibit both pre- and post-emergence activity with a general selectivity toward grasses. Compound Nos. 4 and 5 exhibit outstanding grass herbicide activity and further exhibit grass herbicide activity and selectivity at very low dosages as can be seen from Table 3. (Although only dosage post-herbicidal activity was tested, one would expect the analogy to hold true for pre-emergent activity also.)

TABLE A

[Structure: cyclohexanedione with $R^1$, $R^2$, $R^3$ substituents and NO-CH$_2$-thiophene-$R^6$ oxime ether]

| No. | $R^1$ | $R^2$ | $R^3$ | $R^6$ | m.p. °C. | Carbon Calc. | Carbon Found | Hydrogen Calc. | Hydrogen Found | Nitrogen Calc. | Nitrogen Found |
|---|---|---|---|---|---|---|---|---|---|---|---|
| 1 | CH$_3$CH$_2$— | CH$_3$ | CH$_3$ | H | oil | 62.51 | 59.74 | 6.89 | 7.23 | 4.56 | 4.41 |
| 2 | CH$_3$CH$_2$CH$_2$— | CH$_3$ | CH$_3$ | H | oil | 63.52 | 63.63 | 7.21 | 7.65 | 4.36 | 4.40 |
| 3 | CH$_3$(CH$_2$)$_2$CH$_2$— | CH$_3$ | CH$_3$ | H | oil | 64.45 | 64.91 | 7.51 | 8.03 | 4.17 | 4.01 |
| 4 | CH$_3$CH$_2$— | CH$_3$ | CH$_3$ | Cl | oil | 56.21 | 54.95 | 5.90 | 5.86 | 4.10 | 3.68 |
| 5 | CH$_3$CH$_2$CH$_2$— | CH$_3$ | CH$_3$ | Cl | oil | 57.37 | 57.44 | 6.23 | 6.44 | 3.94 | 3.05 |
| 6 | CH$_3$(CH$_2$)$_2$CH$_2$— | CH$_3$ | CH$_3$ | Cl | oil | 58.45 | 56.44 | 6.54 | 6.42 | 3.79 | 3.25 |
| 7 | CH$_3$CH$_2$CH$_2$— | H | phenyl | Cl | oil | 62.44 | 59.82 | 5.49 | 5.43 | 3.47 | 4.16 |
| 8 | CH$_3$CH$_2$CH$_2$— | H | 4-Cl-phenyl | Cl | 65–68 | 57.54 | 57.14 | 4.83 | 4.84 | 3.20 | 3.27 |

TABLE B

[Structure: cyclohexanedione with $R^1$, gem-dimethyl, and NO-CH$_2$-thiophene with $R^6$, $R^7$, $R^8$ substituents]

| No. | $R^1$ | $R^6$ | $R^7$ | $R^8$ | m.p. °C. | Carbon Calc. | Carbon Found | Hydrogen Calc. | Hydrogen Found | Nitrogen Calc. | Nitrogen Found |
|---|---|---|---|---|---|---|---|---|---|---|---|
| 9 | CH$_3$CH$_2$— | H | H | H | oil | 62.51 | 61.57 | 6.89 | 7.27 | 4.56 | 4.81 |
| 10 | CH$_3$CH$_2$CH$_2$— | H | H | H | oil | 63.52 | 62.76 | 7.21 | 7.55 | 4.36 | 4.51 |
| 11 | CH$_3$(CH$_2$)$_2$CH$_2$— | H | H | H | oil | 64.45 | 63.48 | 7.51 | 7.85 | 4.17 | 3.99 |
| 12 | CH$_3$CH$_2$— | Cl | H | H | oil | 56.21 | 53.32 | 5.90 | 5.73 | 4.10 | 3.96 |
| 13 | CH$_3$CH$_2$CH$_2$— | Cl | H | H | oil | 57.37 | 55.18 | 6.23 | 6.13 | 3.94 | 4.39 |
| 14 | CH$_3$(CH$_2$)$_2$CH— | Cl | H | H | oil | 58.45 | 56.52 | 6.54 | 6.57 | 3.79 | 3.91 |

TABLE C

Position Isomer Mixture Of

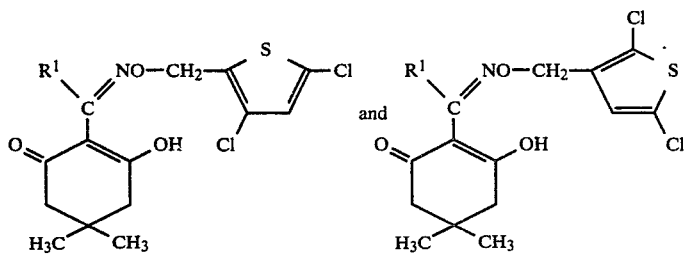

Ratio: 1.5 to 1.0

| No. | R¹ | m.p. °C. | ANALYSIS | | | | | |
|---|---|---|---|---|---|---|---|---|
| | | | Carbon | | Hydrogen | | Nitrogen | |
| | | | Calc. | Found | Calc. | Found | Calc. | Found |
| 15 | CH₃CH₂— | oil | 51.07 | 51.35 | 5.09 | 5.29 | 3.72 | 4.07 |
| 16 | CH₃CH₂CH₂— | oil | 52.31 | 52.82 | 5.42 | 5.67 | 3.57 | 3.77 |

TABLE 1

Pre-Emergence Herbicidal Activity
Dosage: 27 micrograms per cm²

| Compound No. | Broad-Leaf Plants % Phytotoxicity | | | | Grasses % Phytotoxicity | | | |
|---|---|---|---|---|---|---|---|---|
| | Lambs Quarter | Mustard | Pigweed | Soybean | Crab Grass | Water Grass | Wild Oats | Rice |
| 1 | 0 | 0 | 0 | 0 | * | 100 | 40 | 83 |
| 2 | 0 | 0 | 0 | 0 | * | 100 | 70 | 88 |
| 3 | 65 | 0 | 0 | 25 | * | 100 | 40 | 50 |
| 4 | 75 | 73 | 65 | 0 | 100 | 100 | 100 | 100 |
| 5 | 35 | 40 | 35 | 0 | 100 | 100 | 100 | 100 |
| 6 | 30 | 0 | 35 | 0 | 100 | 100 | 100 | 85 |
| 7 | 0 | 0 | 0 | 0 | 100 | 100 | 55 | 10 |
| 8 | 0 | 0 | 0 | 0 | 100 | 88 | 10 | 0 |
| 9 | 30 | 0 | 0 | 10 | 88 | 100 | 33 | 55 |
| 10 | 0 | 0 | 0 | 15 | 98 | 100 | 55 | 62 |
| 11 | 0 | 0 | 30 | 40 | 40 | 60 | 42 | 40 |
| 12 | 0 | 0 | 0 | 20 | 50 | 72 | 38 | 35 |
| 13 | 15 | 20 | 20 | 0 | 70 | 100 | 43 | 43 |
| 14 | 35 | 30 | 55 | 0 | 0 | 50 | 25 | 20 |
| 15 | 35 | 50 | 30 | 0 | 90 | 100 | 35 | 75 |
| 16 | 25 | 43 | 20 | 0 | 98 | 100 | 60 | 70 |

*Neither Control nor Test Plots Germinated

TABLE 2

Post-Emergence Herbicidal Activity
Dosage: 27.5 micrograms per cm²

| Compound No. | Broad-Leaf Plants % Phytotoxicity | | | | Grasses % Phytotoxicity | | | |
|---|---|---|---|---|---|---|---|---|
| | Lambs Quarter | Mustard | Pigweed | Soybean | Crab Grass | Water Grass | Wild Oats | Rice |
| 1 | 0 | 0 | 0 | 0 | 33 | 100 | 100 | 60 |
| 2 | 0 | 0 | 0 | 0 | 50 | 100 | 100 | 80 |
| 3 | 0 | 0 | 0 | 0 | 0 | 0 | 40 | 0 |
| 4 | 50 | 70 | 0 | 30 | 95 | 100 | 100 | 100 |
| 5 | 60 | 65 | 65 | 50 | 90 | 100 | 100 | 100 |
| 6 | 65 | 80 | 80 | 45 | 60 | 90 | 100 | 43 |
| 7 | 0 | 0 | 0 | 0 | 10 | 100 | 100 | 25 |
| 8 | 0 | 0 | 0 | 0 | 0 | 40 | 0 | 0 |
| 9 | 33 | 0 | 25 | 20 | 45 | 70 | 45 | 25 |
| 10 | 60 | 35 | 35 | 0 | 60 | 90 | 55 | 30 |
| 11 | 45 | 35 | 0 | 20 | 15 | 55 | 17 | 0 |
| 12 | 45 | 15 | 30 | 0 | 35 | 65 | 0 | 0 |
| 13 | 30 | 15 | 15 | 25 | 30 | 65 | 25 | 0 |
| 14 | 30 | 48 | 15 | 0 | 30 | 33 | 0 | 0 |
| 15 | 80 | 100 | 53 | 63 | 80 | 95 | 40 | 30 |
| 16 | 85 | 100 | 80 | 60 | 60 | 95 | 80 | 28 |

TABLE 3

Post-Emergence Herbicidal Activity
Low Dosage

| Compound No. | Dosage γ/cm²* | Broad-Leaf Plants % Phototoxicity | | | | Grasses % Phototoxicity | | | |
|---|---|---|---|---|---|---|---|---|---|
| | | Lambs Quarter | Mustard | Pigweed | Soybean | Crab Grass | Water Grass | Wild Oats | Rice |
| 1 | 4.4 | 0 | 0 | 0 | 0 | 0 | 95 | 0 | 10 |
| 1 | 1.8 | 0 | 0 | 0 | 0 | 0 | 33 | 0 | 0 |
| 1 | 0.7 | 0 | 0 | 0 | 0 | 0 | 0 | 0 | 0 |
| 1 | 0.28 | 0 | 0 | 0 | 0 | 0 | 0 | 0 | 0 |
| 2 | 4.4 | 0 | 0 | 0 | 0 | 0 | 83 | 0 | 12 |
| 2 | 1.8 | 0 | 0 | 0 | 0 | 0 | 32 | 0 | 0 |
| 2 | 0.7 | 0 | 0 | 0 | 0 | 0 | 0 | 0 | 0 |
| 2 | 0.28 | 0 | 0 | 0 | 0 | 0 | 0 | 0 | 0 |
| 4 | 4.4 | 0 | 0 | 0 | 0 | 90 | 100 | 92 | 100 |
| 4 | 1.8 | 0 | 0 | 0 | 0 | 33 | 100 | 53 | 95 |
| 4 | 0.7 | 0 | 0 | 0 | 0 | 13 | 99 | 3 | 77 |
| 4 | 0.28 | 0 | 0 | 0 | 0 | 0 | 99 | 0 | 38 |
| 5 | 4.4 | 0 | 0 | 0 | 0 | 42 | 100 | 100 | 97 |
| 5 | 1.8 | 0 | 0 | 0 | 0 | 30 | 100 | 100 | 88 |
| 5 | 0.7 | 0 | 0 | 0 | 0 | 10 | 100 | 98 | 68 |
| 5 | 0.28 | 0 | 0 | 0 | 0 | 0 | 99 | 82 | 40 |
| 6 | 4.4 | 0 | 0 | 0 | 0 | 10 | 77 | 40 | 10 |
| 6 | 1.8 | 0 | 0 | 0 | 0 | 0 | 73 | 30 | 5 |
| 6 | 0.7 | 0 | 0 | 0 | 0 | 0 | 65 | 0 | 0 |
| 6 | 0.28 | 0 | 0 | 0 | 0 | 0 | 40 | 0 | 0 |

*γ/cm² = micrograms per cm²

EXAMPLE 7

In this example, Compound No. 5 of Table A hereinabove was tested for low dosage post-herbicidal activity against an expanded number of grass weeds and grass crops. For comparison purposes, the commercial grass herbicide 2-{1-[prop-2-enyloxy)imino]butyl}-3-hydroxy-5,5-dimethylcyclohex-2-en-1-one was also tested in the same manner. The same test procedure as described in Example 6 was used with the exception of the expanded number of different grass weed and grass crop species. The results of this test are summarized in Tables 4 and 5 hereinbelow.

As can be seen from these results, Compound No. 5 of the present invention exhibited good post-emergence herbicidal activity against Wild Oats at even the low dosages of 0.28 micrograms/cm², and could be safely applied in wheat crops at this dosage. (Note, a wheat phytotoxicity of about 15% or less is considered safe as the wheat will easily grow out of this amount of damage). This spectrum of activity is very important, as Wild Oats is a serious problem to wheat crops. Also, as may be seen from Tables 4 and 5, the comparison herbicide also exhibited low phytotoxicity with respect to wheat but its relative phytotoxicity with respect to wheat and Wild Oats is such that it could not be effectively applied to control Wild Oats at any dosage which is safe for wheat.

TABLE 4

Low Dosage Post-Emergence Grass Herbicidal Activity

| Compound No. | Dosage γ/cm²* | Grasses % Phytotoxicity | | | | | | | | |
|---|---|---|---|---|---|---|---|---|---|---|
| | | Cheatgrass | Johnsongrass | Ryegrass | Switchgrass | Crab Grass | Water Grass | Wild Oats | Yellow Foxtail | Yellow Nutsedge |
| 5 | 4.4 | 23 | 17 | 100 | 98 | 42 | 100 | 100 | 97 | 0 |
| 5 | 1.8 | 18 | 10 | 100 | 96 | 30 | 100 | 100 | 85 | 0 |
| 5 | 0.7 | 0 | 0 | 100 | 82 | 10 | 100 | 98 | 57 | 0 |
| 5 | 0.28 | 0 | 0 | 100 | 32 | 0 | 99 | 82 | 38 | 0 |
| C** | 4.4 | 30 | 75 | 99 | 98 | 98 | 100 | 93 | 100 | 0 |
| C | 1.8 | 10 | 17 | 94 | 95 | 100 | 99 | 45 | 98 | 0 |
| C | 0.7 | 0 | 0 | 75 | 67 | 48 | 88 | 10 | 45 | 0 |
| C | 0.28 | 0 | 0 | 22 | 23 | 13 | 42 | 0 | 37 | 0 |

*γ/cm² = micrograms per cm²
**C = Comparison Compound, i.e., 2-(1-[(prop-2-enyloxy)imino]butyl)-3-hydroxy-5,5-dimethylcyclohex-2-en-1-one

TABLE 5

Low Dosage Post-Emergence Grass Crop Herbicidal Activity

| Compound No. | Dosage γ/cm²* | Grass Crops % Phytotoxicity | | | | |
|---|---|---|---|---|---|---|
| | | Rice | Corn | Oats | Sorghum | Wheat |
| 5 | 4.4 | 97 | 43 | 100 | 12 | 67 |
| 5 | 1.8 | 88 | 10 | 100 | 0 | 30 |
| 5 | 0.7 | 68 | 7 | 97 | 0 | 22 |
| 5 | 0.28 | 40 | 0 | 73 | 0 | 10 |
| C** | 4.4 | 83 | 100 | 98 | 47 | 45 |
| C | 1.8 | 12 | 95 | 90 | 12 | 13 |
| C | 0.7 | 0 | 47 | 33 | 0 | 3 |
| C | 0.28 | 0 | 12 | 2 | 0 | 0 |

*γ/cm² = micrograms per cm²
**C = Comparison Compound, i.e., 2-(1-[(prop-2-enyloxy)imino]butyl)-3-hydroxy-5,5-dimethylcyclohex-2-en-1-one Obviously, many variations and modifications of the invention, described hereinabove and below, can be made without departing from the essence and scope thereof.

What is claimed is:

1. A compound selected from the group having the formula:

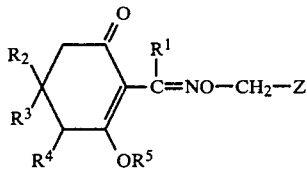

wherein
R¹ is hydrogen or lower alkyl;
R² and R³ are independently selected from the group consisting of hydrogen, lower alkyl, aryl having 6 through 10 carbon atoms, substituted aryl having 6 through 10 carbon atoms, and 1 through 4 substituents independently selected from the group consisting of fluoro, chloro, bromo, iodo, and trifluoromethyl;
R⁴ is hydrogen or alkoxycarbonyl having 2 through 4 carbon atoms;
R⁵ is hydrogen; and
Z is a group having the formula:

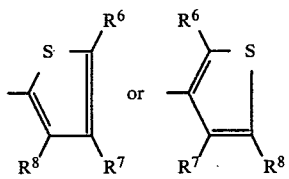

wherein R⁶, R⁷, and R⁸ are independently selected from the group of hydrogen, halo, nitro, alkyl having 1 through 4 carbon atoms, alkoxy having 1 through 4 carbon atoms, or trifluoromethyl; and cation salts thereof.

2. The compound of claim 1 wherein one of R⁶, R⁷, or R⁸ is halo or trifluoromethyl and the other two are each hydrogen.

3. The compound of claim 1 wherein one of R⁶, R⁷, or R⁸ is chloro and the other two are each hydrogen.

4. The compound of claim 1 wherein R¹ is propyl.

5. The compound of claim 1 wherein R² and R³ are independently selected from the group consisting of lower alkyl.

6. The compound of claim 5 wherein R² and R³ are each methyl.

7. The compound of claim 1 wherein one of R² or R³ is hydrogen and the other is said aryl or said substituted aryl.

8. The compound of claim 1 wherein Z is the group having the formula:

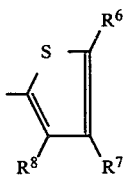

wherein R⁶, R⁷, and R⁸ are as defined in claim 1.

9. The compound of claim 8 wherein one of R⁶, R⁷, or R⁸ is chloro and the other two are each hydrogen.

10. The compound of claim 9 wherein R¹ is propyl.

11. The compound of claim 10 wherein one of R² or R³ is hydrogen and the other is phenyl or substituted phenyl having one or two substituents independently selected from the group of halo and trifluoromethyl.

12. The compound of claim 10 wherein one of R² or R³ is hydrogen and the other is phenyl.

13. The compound of claim 10 wherein R² and R³ are each methyl and R⁴ is hydrogen.

14. The compound of claim 13 R⁶ is chloro.

15. The compound of claim 1 wherein Z is the group having the formula:

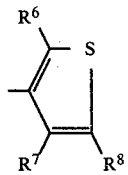

wherein R⁶, R⁷, and R⁸ are as defined in claim 1.

16. The compound of claim 15 wherein one of R⁶, R⁷, or R⁸ is chloro and the other two are each hydrogen.

17. The compound of claim 16 wherein R¹ is propyl.

18. The compound of claim 17 wherein one of R² or R³ is hydrogen and the other is phenyl or substituted phenyl having one or two substituents independently selected from the group of halo and trifluoromethyl.

19. The compound of claim 17 wherein one of R² or R³ is hydrogen and the other is phenyl.

20. The compound of claim 17 wherein R² and R³ are each methyl.

21. A method for controlling grasses which comprises applying an herbicidally effective amount of a compound of claim 1 to the foliage of such grasses.

22. A pre-emergence method for controlling grasses which comprises applying an herbicidally effective amount of a compound of claim 1 to the potential growth medium of such grasses.

23. An herbicidal composition which comprises a grass herbicidally effective amount of a compound of claim 1 and a compatible carrier.

24. A method for controlling grasses which comprises applying an herbicidally efective amount of a compound of claim 14 to the foliage of said grasses.

25. A pre-emergence method for controlling grasses which comprises applying an herbicidally effective amount of a compound of claim 14 to the potential growth medium of said grasses.

26. An herbicidal composition which comprises a grass herbicidally effective amount of a compound of claim 14 and a compatible carrier.

27. The compound of claim 1, 8, or 15 wherein R⁴ is hydrogen.

28. The compound of claim 1, 8, or 15 wherein R⁴ is alkoxycarbonyl having 2 through 4 carbon atoms.

* * * * *